United States Patent [19]

Olsson

[11] Patent Number: 5,066,655

[45] Date of Patent: Nov. 19, 1991

[54] N6-SUBSTITUTED 9-METHYLADENINES: A NEW CLASS OF ADENOSINE RECEPTOR ANTAGONISTS

[75] Inventor: Ray A. Olsson, Tampa, Fla.

[73] Assignee: Whitby Research, Inc., Irvine, Calif.

[21] Appl. No.: 424,293

[22] PCT Filed: Apr. 25, 1988

[86] PCT No.: PCT/US88/01405

§ 371 Date: Oct. 6, 1989

§ 102(e) Date: Oct. 6, 1989

[87] PCT Pub. No.: WO88/08303

PCT Pub. Date: Nov. 3, 1988

[51] Int. Cl.$^5$ ............................................. A61K 31/52
[52] U.S. Cl. ..................................... 514/261; 514/81; 544/244; 544/277
[58] Field of Search .................. 544/277; 514/261, 81

[56] References Cited

U.S. PATENT DOCUMENTS

| | | | |
|---|---|---|---|
| 2,881,164 | 4/1959 | Kissman et al. | 260/211.5 |
| 3,502,649 | 3/1970 | Thiel et al. | 260/211.5 |
| 3,509,129 | 4/1970 | Kampe et al. | 260/211.5 |
| 3,796,700 | 3/1974 | Yoshioka et al. | 260/211.5 |
| 3,851,056 | 11/1974 | Stork et al. | 424/180 |
| 3,901,876 | 8/1975 | Vorbruggen | 260/211.5 |
| 3,929,763 | 12/1975 | Fauland et al. | 260/211.5 |
| 4,029,884 | 6/1977 | Stein et al. | 536/26 |
| 4,081,534 | 3/1978 | Elion et al. | 424/180 |
| 4,090,021 | 5/1978 | Vorbruggen | 436/28 |
| 4,167,565 | 9/1979 | Stein et al. | 424/180 |
| 4,224,438 | 9/1980 | Fauland et al. | 536/26 |
| 4,495,180 | 1/1985 | Alexander | 514/46 |
| 4,514,405 | 4/1985 | Irmscher et al. | 514/46 |
| 4,798,833 | 1/1989 | Johansson et al. | 544/277 |

FOREIGN PATENT DOCUMENTS

| | | | |
|---|---|---|---|
| 2007273 | 2/1970 | Fed. Rep. of Germany | 544/277 |
| 2081524 | 3/1971 | France | 544/277 |
| 2195434 | 8/1974 | France | 544/277 |
| 58-167599 | 10/1983 | Japan | 544/277 |
| 58-167600 | 10/1983 | Japan | 544/277 |
| 1123245 | 8/1968 | United Kingdom | 544/277 |
| 2077726 | 12/1981 | United Kingdom | 544/277 |

OTHER PUBLICATIONS

Chemical Abstracts 100:68653d (1984), Stein et al., Annals New York Acad. Sci., 255, 380–389 (1975).
Prasad et al., J. Med. Chem. 23(3), 313–319 (1980).
Stein, H., J. Med. Chem. 16(11), 1306–1308 (1973).
Schwabe, U1, In Berne et al., Ch. 6 of "Regulatory Function of Adenosine", 77–96 (1983).
Fox et al., J. Biol. Chem. 258(11), 6952–6955 (1983).
Daly, J. E., J. Med Chem, Perspective 25(3) (1982).
Republic of South Africa Patent Journal, vol. 1 (1958), 202–203.
Olsson et al., "Coronary Vasoctivity of Adenosine in the Conscious Dog", Circulation Research (1979), vol. 45, 468–478.

Primary Examiner—Mary C. Lee
Assistant Examiner—Robert Whittenbaugh
Attorney, Agent, or Firm—Walter A. Hackler; Robert J. Baran

[57] ABSTRACT

A series of 15 N$^6$-substituted 9-methyladenines have been assessed as antagonists of A$_2$-adenoisine receptor-mediated stimulation of adenylate cyclase in membranes of human platelets and rat PC12 cells and of A$_1$-adenosine receptor-mediated inhibition of adenylate cyclases in membranes of rat fat cells and as inhibitors of binding of N$^6$-R-[$^3$H]-phenylisopropyladenosine to A$_1$ adenosine receptors in rat brain membranes.

4 Claims, No Drawings

N6-SUBSTITUTED 9-METHYLADENINES: A NEW CLASS OF ADENOSINE RECEPTOR ANTAGONISTS

SUMMARY OF THE INVENTION $N^6$-substitution can markedly increase potency of 9-methyladenine at $A_1$ receptors, while having lesser effects or even decreasing potency at $A_2$ receptors. Effects of $N^6$ substituents on adenosine receptor activity of the 9-methyladenines are reminiscent of effects of $N^6$-substituents on activity of adenosine, suggesting that $N^6$-substituted 9methyladenines bind to adenosine receptors in the same orientation as do $N^6$-substituted adenosines. $N^6$-Cyclopentyl -9-methyladenine is more potent than 9-methyladenine.

$N^6$-Cyclopentyl and several other $N^6$-alkyl and $N^6$ cycloalkyl analogs are selective for $A_1$ receptors while 9-methyladenine is the most $A_2$-receptor selective antagonist. The $N^6$-R- and $N^6$-S-(1-phenyl-2-propyl)-9-methyladenines, analogous to $N^6$-R- and $N^6$-S-phenylisopropyladenosine, exhibit stereoselectivity at both $A_1$ and $A_2$ receptors.

DETAILED DESCRIPTION OF THE INVENTION

The compounds of this invention are represented by the general formula:

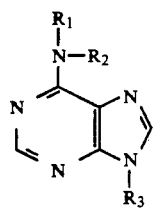

wherein $R_1$ is selected from the group consisting of cycloalkyl radicals having from 3 to 7 ring carbon atoms, alkyl radicals having from 2 to 10 carbon atoms, aryl radicals having from 6 to 10 carbon atoms, aralkyl radicals having from 7 to 10 carbon atoms and heteroatom substituted derivatives thereof wherein said heteroatom may be selected from the group consisting of halogen, nitrogen, phosphorus, sulfur and oxygen; $R_2$ may be hydrogen or $R_1$, and $R_3$ is an alkyl group comprising from 1 to 4 carbon atoms.

Preferably the compounds are those wherein $R_3$ is methyl; wherein $R_2$ is hydrogen; wherein $R_1$ is a cycloalkyl having from 4 to 6 carbon atoms in the ring, more preferably phenyl or a substituted phenyl such as 0-fluorophenyl, 3,4,5-trimethoxyphenyl, benzyl, phenethyl, 2-(3pyridylethyl), 2-(3-thienylethyl), or 3-pentyl; or wherein $R_2$ is selected from the group consisting of methyl and 2-propyl and $R_1$ is selected from the group consisting of cyclopentyl and phenyl. Most preferably $R_1$ is a norbornane.

The preparation of 9-methyl adenines is well known. See R. K. Robins, K. J. Dille, and B. E. Christensen, *J. Org. Chem.*, 19, 930 (1954); R. K. Robins and H. H. Lin, *J. Am. Chem. Soc.*, 79, 490 (1975; and J.A. Montgomery and Carroll Temple, Jr., *J. Am. Chem. Soc.*, 79, 5238 (1957).

To prepare $N^6$-cyclopentyl-9-methyl Adenine the following additional steps were taken. A mixture of 6-chloro-9-methyl Adenine (0.82 g), cyclopentylamine (0.52 ml), triethylamine (0.53 ml) and ethanol (60 ml), was refluxed for 24 hours. The solution was concentrated in vacuo to a yellow syrup. The syrup was passed through a C-18 column to give 0.78g or 74% yield of with m.p. - 108–109° C. $^1$HNMR(Me$_2$SO-d6): δ1-2(m,9 H); 3.7(S,CH$_3$); 7.6(d,NH); 8.1(S,1H); 8.2(S,1H).

To prepare $N^6$ 3-pentyl-9-methyladenine the following steps were taken. A mixture of 6-chloro-9-methyladenine (1.5 g), 3-pentylamine (1.3 ml), triethylamine (1.3 ml) and ethanol (60 ml), was refluxed for 24 hours. The solution was concentrated and passed through a C-18 column to give a white solid having m.p. - 107–109° C.

To prepare $N^6$-(2-Aminonorbornanyl)-9-methyl Adenine the following additional steps were taken. A mixture of 1.5 g 6-chloro-9-methyl Adenine, 1.75 g 2-aminonorbornane, 2.9 ml triethylamine and 60 ml ethanol was refluxed overnight. The solution was then concentrated in vacuo and the remainder was passed through C-18 prep-chromatography to give 1.6 g (75% yield) m.p. 130–131° C. $^1$HNMR(Me$_2$SO-d6): δ1 -2.6(m,10 H); 3.8(S, CH$_3$); 4.1(m,1H); 7.2(S,NH); 7.4(S,1H); 7.6(S,1H).

Adenosine receptors have been divided into two subtypes, based on adenylate cyclase activity; $A_1$ ($n_1$) receptors mediate inhibition and $A_2$ ($R_a$) receptors mediate stimulation of adenylate cyclase activity (for reviews see ref. 1., 2). Some $N^6$-substituted adenosine analogs like $N^6$-R-1-phenyl-2-propyladenosine (R-PIA) have very high affinity for $A_1$ adenosine receptors, while 5'-N-ethylcarboxamido-adenosine (NECA) is more potent than $N^6$-substituted analogs at $A_2$ receptors. Alkylxanthines, such as caffeine and theophylline, are the best known antagonists at adenosine receptors. Adenine was generally believed to have no effect on adenosine receptor-controlled systems. However, adenine is specific, competitive antagonist of adenosine-induced cyclic AMP accumulation in a human fibroblast cell line with A $K_i$ of 200 μM (3). Methylation of adenine at the 9-position increases potency about 4-fold. A variety of $N^6$ -substituted-9-methyladenine derivatives have now been prepared and tested in three adenylate cyclase-coupled adenosine receptor systems. For $A_2$ adenosine receptors human platelets and rat pheochromocytoma (PC12) cells and for $A_1$ binding site for [$^3$H]$N^6$-R-1-phenyl-propyladenosine ([$^3$H]PIA) was determined in rat brain membranes. Certain of the $N^6$-substituted 9-methyladenines proved to be potent antagonists at adenosine receptors and some showed selectivity for either $A_1$ or $A_2$ receptors.

The invention is further illustrated by the following examples which are illustrative of various aspects of the invention, and are not intended as limiting the scope of the invention as defined by the appended claims.

The synthesis and the chemical properties of the adenine and hypoxanthine derivatives will be described elsewhere. [α-$^{32}$P]ATP (40 Ci/mmol) was purchased from Amersham (Arlington Heights, IL, USA). [$^3$H]$N^6$-R-1-Phenyl -2-propyladenosine ([$^3$H]PIA, 49.9 Ci/mmol) was purchased from New England Nuclear, Boston, MA. USA). Other compounds used in this study were from standard sources as described (4).

Human platelet, rat pheochromocytoma (PC12) cell, rat fat cell and rat cerebral cortex membranes were prepared as described (4,5,6). Adenylate cyclase activity and binding [$^3$H]PIA to cerebral cortex membranes were determined essentially as described (4,5,6). $K_B$ values for the compounds were determined as described (4). Briefly stated, concentration-response curves of NECA for the stimulation of adenylate cyclase of PC12 cell and platelet membranes and of R-PIA for the inhibition of isoproterenol-stimulated adenylate cyclase activity in fat cell membranes in the absence and presence of the adenine derivative were done using at least 7 concentrations of the agonist. $EC_{50}$ and $IC_{50}$ values for the agonists were obtained from the concentration-response curves by linear regression after logit-log transformation. $K_B$ values of the antagonists were calculated using the Schild equation $K_B = C/(CR-1)$, where C denotes the concentration of the competitor and CR the ratio of the $EC_{50}$ and $IC_{50}$ values in the presence and absence, respectively, of the competitor. $IC_{50}$ of the compounds for inhibition of [$^3$H]PIA binding to cerebral cortex membranes were transformed into $K_i$ values as described (6).

RESULTS

$A_2$ Adenosine Receptors

The effects of adenine and adenine analogs on $A_2$ receptor were studied in human platelets. In these cells, $A_2$ receptor-mediated stimulation of adenylate cyclase results in an inhibition of aggregation (5,7).

Adenine (compound Example 1) itself does not affect basal adenylate cyclase activity (data not shown), but antagonizes the NECA-induced stimulation of adenylate cyclase activity. However, adenine (Example 1) is a very weak antagonist at $A_2$ receptors of platelets.

Incorporation of a methyl group at the 9-position of the adenine molecule results in a marked increase in potency. Thus, 9-methyladenine (Example 2) is more potent than the adenine itself at $A_2$ receptors of platelets.

Substituents at the $N^6$-position of 9-methyladenine (Example 2) markedly influence the antagonist potency at the platelet $A_2$ receptor. The $N^6$-cycloalkyl analogs (Examples 3,4,6) are more potent than 9-methyladenine itself.

Incorporation of an additional methyl group into $N^6$-cyclopentyl-9-methyladenine (Example 4) so as to yield a tertiary carbon at the $N^6$-nitrogen reduces potency with $N^6$-(1-methylcyclopentyl)-9-methyladenine (Example 5) being less potent than the parent cyclopentyl analog (Example 4). The $N^6$-methyl analog (Example 7) is much less potent than 9-methyladenine at the platelet receptor, while the $N^6$-3pentyl analog (Example 8) is more potent. The $N^6$-phenyl analog (Example 9) is equipotent to 9-methyladenine. The presence of ortho-fluoro moiety in compound Example 10 increases potency at the platelet $A_2$ receptor. The $N^6$-benzyl and $N^6$-(2-phenethyl analog) (Examples 11,12) are less potent than 9-methyladenine at the platelet receptors. $N^6$-2-(3,4,5 trimethoxyphenyl-ethyl-9-methyladenine (Example 13) is as potent as 9-methyladenine. The heteroaryl analog $N^6$-2-(3-pyridylethyl)-9-methyladenine (Example 14) is less potent than 9-methyladenine, while another heteroaryl analog $N^6$-2-(3-thienylethyl)-9-methyladenine (Example 15) is somewhat more potent. The $N^6$-1-phenyl-2-propyl derivatives are analogs containing a chiral carbon attached to the $N^6$-nitrogen: The R-isomer (Example 16) is more potent than the S-isomer (Example 17). The $O^6$-phenyl derivatives of 9-methylhypoxanthine (Examples 18-21) are very weak or inactive as inhibitors of NECA-induced stimulation of adenylate cyclase activity of human platelet membranes.

The potencies of the adenine derivatives are determined in a similar manner for $A_2$ receptors of rat pheochromocytoma (PC12) cells (4,8,9), using antagonism of the NECA-induced stimulation of adenylate cyclase activity of the PC12 cells membranes to assess antagonist potencies.

While there are similarities, there are also some notable differences in the structure-activity relationship for the adenines at $A_2$ receptors of platelets of PC12 cells.

As was the case for the platelet system, adenine (Example 1) is a very weak antagonist of the NECA-stimulated adenylate cyclase in PC12 cell membranes. 9-methyladenine (Example 2) is equally potent at $A_2$ receptors of human platelets and rat PC12 cells.

In contrast to the results with platelets, incorporation of $N^6$-substituents into 9-methyladenine does not in any case increase the potency of the 9-methyladenine at the $A_2$ receptor of PC12 cells:

Potencies of all of the $N^6$-substituted 9-methyladenines at $A_2$ receptors of PC12 cells are either the same as or lower than that of the parent compound.

In certain cases, namely the $N^6$-cyclopentyl (Example 4), $N^6$-3-pentyl (Example 8) and $N^6$-phenyl (Example 9) analogs, the analog is more potent at the platelet $A_2$ receptor than at the PC12 $A_2$ receptor. In no case is the $N^6$-substituted 9-methyladenine less potent at the platelet $A_2$ receptor than at the PC12 A2 receptor. Incorporation of an additional methyl to yield the tertiary analog $N^6$-1-methylcyclopentyl-9-methyladenine (Example 5) reduces potency in PC12 cells.

The O6-phenyl-9-methylhypoxanthines (Examples 18-21) are nearly inactive in both cell types.

$A_1$ Adenosine Receptors

Rat fat cells were used for evaluation of structure-activity relationships of adenine derivatives at adenylate cyclase-coupled $A_1$-adenosine receptors. In these cells, adenosine analogs cause an inhibition of adenylate cyclase activity and lipolysis (10).

Adenine (Example 1) itself does not affect R-PIA-induced inhibition of fat cell adenylate cyclase activity. 9-Methyladenine (Example 2) antagonizes the effect of R-PIA.

Incorporation of cycloalkyl or alkyl substituents into the $N^6$-position of 9-methyladenine (Example 2) can markedly increase the antagonistic potency at the fat cell $A_1$ receptor. Thus, the $N^6$-cycloalkyl-9-methyladenines (Examples 3,4,6) are more potent than the parent compound 9-methyladenine and $N^6$-3-pentyl-9-methyladenine (Example 8) is more potent than the aprent compound at $A_1$ receptors of fat cells. $N^6$-Methylcyclopentyl-9-methyladenine (Example 5) is less potent than the $N^6$-cylcopentyl analog (Example 4). The $N^6$-methyl analog (Example 7) is less potent than 9-methyladenine. The two $N^6$-phenyl analogs (Example 9,10) are more potent than 9-methyladenine in the fat cell.

The $N^6$-2-phenethyl (Example 12) analog is much less potent. Of the phenethyl (Examples 12,13) and heteroarylethyl (Examples 14,15) analogs only the $N^6$-2-(3-thienyl-ethyl)-9-methyladenine is more potent than 9-methyladenine itself in the fat cell. The R- and S-isomers of $N^6$-1-phenyl-2-propyl-9-methyladenine (Examples 16,17) are more potent than the parent compound at $A_1$ receptors of fat cells. The $O^6$-phenyl-9-methylhypoxanthines (Examples 18-2) are very weak or inactive as antagonists in fat cell membranes.

Similar results are obtained when the $K_i$-values of the adenine derivatives for inhibition of [$^3$H]PIA binding to rat cerebral cortex membranes were determined. The low potency of adenine (Example 1) is commensurate with the results from the fat cell adenylate cyclase assay. 9-Methyladenine (Example 2) is equally potent at $A_1$ receptors of fat cells and cerebral cortex. The $K_i$-values of the $N^6$ substituted 9-methyladenine derivatives for inhibition of radioligand binding in brain membranes are lower than the corresponding $K_B$-values from the fat cell adenylate cyclase. As in the case with fat cells, $N^6$-cyclopentyl-9-methyladenine (Example 4) is more potent than the $N^6$-methylcyclopentyl analog (Example 5). The 2-phenethyl (Examples 12,13) analogs are very weak antagonists of [$^3$H]PIA binding in rat brain membranes as expected from results with fat cell adenylate cyclase. $N^6$-R-1-Phenyl-2propyl-9-methyladenine (Example 16) is more potent than the S-isomer (Example 17). The $O^6$-phenyl-9-methylhypoxanthinederivatives (Examples 18–21) only marginally inhibit [$^3$H]PIA binding.

Discussion

Xanthines, the major structural class of antagonists for adenosine receptors, have a planar heterocyclic ring system analogous to the heterocyclic purine (adenine) ring of adenosine. It has been proposed that the site in adenosine receptors that interacts with the adenine ring of adenosine also interacts with the xanthine ring of such adenosine antagonists as theophylline and caffeine (2). A variety of other compounds containing a planar heterocyclic ring have antagonistic activity at adenosine receptors. These include pyrazolopyrimidines (11), pyrazolopyridines (12,13), mesoionic xanthine analogs (14), benzopteridines (3), and 9-methyladenine (3). The last heterocycle 9methyladenine, because of the identity of the heterocyclic ring with that of adenosine, seems even more likely than other heterocycles to bind at the same "heterocycle" site as do the adenosines. The present study was designed to test the premise that, as in the case of adenosine, $N^6$-substituents on 9-methyladenine would alter activity of the 9-methyladenines in the same way as $N^6$-substituents alter the activity of adenosines. The topography of binding site for $N^6$-substituents in both $A_1$ and $A_2$ adenosine receptors has been extensively investigated (see 9, 16 and ref. therein). The binding site for $N^6$-substituents differs significantly for $A_1$ receptors compared to $A_2$ receptors. At the $A_1$ receptors, $N^6$-substituents can markedly enhance activity. The steroselectivity for compounds such as R-PIA and S-PIA that contain chiral $N^6$-substituents is a well-known characteristic of $A_1$ receptors. At the $A_2$ receptors, most $N^6$-substituents reduce activity of adenosine and steroselectivity is less pronounced than at $A_1$ receptors. Certain $N^6$-substituents do markedly enhance activity of 9-methyladenine at $A_1$ receptors. The $N^6$-cycloalkyl-9-methyladenines (Ex. 3, 4, 6) are the most potent of $N^6$-substituted 9-methyladenines at $A_1$ receptors.

Similarly, $N^6$-cycloalkyladenosines are among the most potent $N^6$-substituted adenosines of $A_1$ receptors (9). Introduction of an additional methyl to $N^6$-cyclopentylmethyladenine (Ex. 4) to yield $N^6$-1-methylcyclopentyl 9methyladenine (Ex. 5) reduces activity at $A_1$ receptors. Similarly, activity of the $N^6$-(1-methylcyclopentyl)adenosine at $A_1$ receptors is reduced compared to $N^6$-cyclopentyladenosine (9). The only $N^6$-alkyl or $N^6$-cycloalkyl substituent that reduces activity of 9methyladenines at $A_1$ receptors is methyl, reminiscent of the low activity of $N^6$-methyladenosine at $A_1$ receptors (9). The modest activity of $N^6$-benzyl-9-methyladenine (Ex. 11) is also consonant with the low activity of $N^6$-benzyladenosine at $A_1$ receptors (9).

The R- and S-enantiomers of $N^6$-(1-phenyl-2-propyl)-9-methyladenine, analogous to R- and S-PIA, these analogs are true enantiomers, since the other chiral centers of the ribose moiety are absent. It should be noted that the stereoselectivity of the 9-methyladenine analogs at $A_1$ receptors is much less than the stereoselectivity of R- and S-PIA at $A_1$ receptors (9).

The results indicate that 9-methyladenines show effects of $N^6$-substituents on activity at $A_1$ receptors similar to, but not identical with the effects of $N^6$-substituents on agonist activity of the four $O^6$-phenyl substituted-9-methylhypoxanthines is reminiscent of the inactivity of purine ribosides containing oxygen or sulfur in place of nitrogen at the 6-position at adenosine receptors (15).

At $A_2$ receptors, $N^6$-substituents have much smaller effects on activity of 9-methyladenine than was the case with $A_1$ receptors. Indeed, many substituents have no effect or reduce activity. The two $A_2$ receptors do not appear identical in terms of interaction with the $N^6$-substituted 9-methyladenines. Whether such differences are related to species or tissue are unknown. Certainly, brain $A_1$ receptors differ markedly in agonist/antagonist activity in different species (16). At the $A_2$ receptor of human platelets the cycloalkyl-, 3-pentyl-, 2-fluorophenyl-, 2-(3-thienylethyl)-and R-1-phenyl-2-propyl-substituents enhance activity. Certain $N^6$-substituted adenosines corresponding in structure to the $N^6$-substituted 9-methyladenines have been investigated as agonists at platelet $A_2$ receptors (9). There was only a modest range of potency with the $N^6$-cyclobutyl-, $N^6$-cyclohexyl-, $N^6$-2-(3-thienylethyl)- and $N^6$-benzyl-adenosines and R-PIA being the more potent of the $N^6$-substituted adenosines. Thus, the results with $N^6$-substituted 9-methyladenines at platelet $A_2$ receptors would not have been predicted from the effects in the analogous adenosines. At the $A_2$ receptors of PC12 cells, none of the $N^6$-substituents increased activity relative to 9-methyladenine itself Indeed, certain substituents decreased activity. Again, these effects would not have been predicted from the agonist activity of the analogous $N^6$-substituted adenosines at $A_2$ receptors of PC12 cells (9): As for the platelet $A_2$ receptor there was not a wide range of potencies for the adenosines at PC12 receptors with the $N^6$-cyclobutyl-, R-PIA, $N^6$-2-phenethyl-, $N^6$-cyclohexyl, -$N^6$-2-(3-pyridylethyl)- and $N^6$-2-(3,4,5-trimethoxyphenylethyl)-analogs being the more potent of the series. Thus, the effects of $N^6$-substitution on activity of 9-methyladenines and adenosines at $A_2$ receptors are not identical, perhaps reflecting the lack of major positive contributions of such substituents to activity at $A_2$ receptors. It is of interest that data on both the antagonist series of $N^6$-substituted adenine and the agonist series of $N^6$-substituted adenosines (9) provide evidence for the lack of identity of $A_2$ receptors in platelets and PC12 cells. The $O^6$-phenyl-9-methylhypoxanthines are inactive or nearly so at the $A_2$ receptors, as is the case with 6-phenoxypurine riboside at coronary $A_2$ receptors (17).

Certain of the $N^6$-substituted 9-methyladenines are selective for receptors, in particular $N^6$-cyclo-butyl, cyclopentyl-, 1-methylcyclopentyl-, and cyclohexyl analogs, while 9-methyladenine and $N^6$-2-(3, 4, 5-trimethoxyphenylethyl)-9-methyladenine exhibit a selectivity for $A_2$ receptors.

It is known that $A_1$ receptors influence inhibition of adenylate cyclase in fat brain and heart cells; whereas $A_2$ receptors influence stimulation of adenylate cyclase in endothelial and smooth muscle cells. (See John W. Daly, et al., "Structure - Activity Relationship for $N^6$-Substituted Adenosines at a Brain $A_1$-Adenosine Receptor With A Comparison to an $A_2$-Adenosine Receptor Regulating Coronary Blood Flow," Biochemical Pharmacology, Vol. 35. No. 15, pp. 2467–2471 (1986)).

To prove the selectivity of these compounds, in vitro assays were conducted utilizing model tissues that are thought to contain homogenous populations of either the $A_1$ or $A_2$ adenosine receptor The drugs were characterized by their ability to antagonize competitively the action of adenosine agonists in eliciting two responses the reduction in force of contraction of guinea pig atrium ($A_1$); and the decrease in the contractile tone of the guinea pig taenia caecum ($A_2$).

The left atria from male guinea pigs were isolated, suspended between two punctate electrodes, and placed in a 20 ml organ bath that contained Krebs-Hensileit solution that was continuously gassed with 95% $O_2$ + 5% $CO_2$ and maintained at 31° C. The resting tension was one gram. Theatria were stimulated electrically at 1 hz, 1 ms duration pulses at supramaximal voltage. The force of contraction was recorded isometrically.

Taenia from the guinea pig caecum were cut into lengths of 1.5–2 cm. The tissues were suspended in a 20 ml organ bath containing de Jalon's solution that was gassed with 95% $O_2$ + 5% $CO_2$ and maintained at 31° C. The resting tension was 1.5 g. The contractile response was measured isotonically. Tissues were contracted with $10^{-7}M$ 5-methylfurmethide and allowed sufficient time to reach a stable contraction before addition of adenosine agonists The ability of the compounds to antagonize the effects of agonists was analyzed using modified Schild plots.

Although there was some sensitization of the tissue, i.e. addition of the agonist produced a larger response in the presence of high concentrations of the subject compounds, Examples 8, 4 and 22 did not competitively antagonize the effects of adenosine agonists in relaxing the taenia caecum. There was some sensitization of the tissue. This sensitization effect is also observed when using high concentrations of 8-phenyltheophylline (8-PT), a nonselective adenosine receptor antagonist. 8-PT did antagonize the effects of agonists at low concentrations. The lack of competitive antagonism suggests that the compounds tested do not interact appreciably with $A_2$-adenosine receptors.

However, Examples 8, 4, 22 and 23 all were found to be competitive antagonists at adenosine receptors in the atria. Examples 8 and 23 also produced increases in basal force of contraction in the atria. Affinity constants ($pK_B$) were determined for the present compounds using known methods and were as follows.

| Drug | $pK_B$ |
| --- | --- |
| Ex. 8 | 5.4 ± 0.14 |
| Ex. 4 | 6.17 ± 0.11 |
| Ex. 22 | 6.28 ± 0.09 |
| Ex. 23 | 5.36 ± 0.1 |

These results show that the compounds of the invention display selectivity towards the $A_1$ adenosine receptor, with Ex. 22 being the most potent antagonist.

In vitro selectivity of the present antagonists was confirmed by in vivo tests on rate heart rate and blood pressure, the former associated with $A_1$ receptors and the latter associated with $A_2$ receptors.

Rats were anesthetized with urethan and blood pressure was monitored via a carotid cannula. Drug injections were made intravenously through a jugular cannula. Blood pressure, EGC, and heart rate were recorded on a Grass polygraph.

Adenosine produced a dose dependent decrease in blood pressure and heart rate, with a concomitant increase in the P-R interval of the ECG. Administration of $N^6$-(endo norbornyl)-9-methyladenine attenuated the effects of subsequently administered adenosine on all parameters measured. At high doses, adenosine causes heart block; this effect was also substantially reduced by the agonist due to the short duration of action and route of administration of adenosine, it is often difficult to determine whether adenosine decreased blood pressure by causing peripheral vasocilation or by reducing cardiac output. Therefore NECA (5'-N-ethylcarboxamide adenosine) was used as an adenosine agonist due to its longer duration of action and $A_2$adenosine receptor selectivity. Prior administration of N-0861 attenuated the effects of NECA on the heart while minimally affecting the NECA-induced decrease in blood pressure. These results show that $N^6$-endo norbornyl)-9-methyladenine is a cardioselective adenosine receptor antagonist in vivo and support the date above showing selectively of the N-6 substituted 9 methyladenine as $A_1$ adenosine receptor antagonists.

Further investigation of this new class of adenosine receptor antagonists both in vitro and in vivo will be required to establish their usefulness in definition and elucidation of functions of adenosine receptors.

| Example No. | Compound |
| --- | --- |
| 1 | Adenine |
| 2 | 9-Methyladenine-(9-MA) |
| 3 | $N^6$-Cyclobutyl-9-MA |
| 4 | $N^6$-Cyclopentyl-9-MA |
| 5 | $N^6$-Methylcyclopentyl-9-MA |
| 6 | $N^6$-Cyclohexyl-9-MA |
| 7 | $N^6$-Methyl-9-MA |
| 8 | $N^6$-3-Pentyl-9-MA |
| 9 | $N^6$-Phenyl-9-MA |
| 10 | $N^6$-2-Fluorophenyl-9-MA |
| 11 | $N^6$-Benzyl-9-MA |
| 12 | $N^6$-2-Phenethyl-9-MA |
| 13 | $N^6$-2-(3,4,5-Trimethoxyphenylethyl-9-MA |
| 14 | $N^6$-2-(3-Pyridylethyl)-9-MA |
| 15 | $N^6$-2-(3-Thienylethyl)-9-MA |
| 16 | $N^6$-R-1-Phenyl-2-propyl-9-MA |
| 17 | $N^6$-S-1-Phenyl-2-propyl-9-MA |
| 18 | $O^6$-Phenyl-9-Methyhypoxanthine (9MH) |
| 19 | $O^6$-(2-Fluorophenyl)-9-MH |
| 20 | $O^6$-(3-Fluorophenyl)-9-MH |
| 21 | $O^6$-(4-Fluorophenyl)-9-MH |
| 22 | $N^6$-(endo norbornyl)-9-MA |
| 23 | $N^6$-4-(-2-thienyl)-3-butyl)-9-MA |
| 24 | $N^6$-(exo norbornyl)-9-MA |

References (1) Daly, J. W. (1982) J. Med. Chem. 25, 197–207.

(2) Daly, J.W. (1985) In: Advances in Cyclic Nucleotide and Protein Phosphorylation Research (D. M. F. Cooper and K. B. Seamon, eds), Volume 19, Raven Press, New York, pp. 29–46.

(3) Bruns, R. F. (1981) Biochem. Pharmacol. 30, 325-333.

(4) Ukena, D., Daly, J. W., Kirk, K. L., and Jacobson, K. A. (1986) Life Sci. 38, 797-807.

(5) Ukena, D., Boehme, E., Schwabe, U. (1984) Naunyn-Schmiedebert's Arch. Pharmacol. 327, 36-42.

(6) Jacobson, K. A., Ukena, D., Kirk, K. L., and Daly, J. W. (1986) Proc. Natl. Acad. Sci. USA 83, 4089-4093.

(7) Cusack, N. J. and Hourani, S. M. (1981) Br. J. Pharmacol. 72, 443-447.

(8) Ukena, D., Shamin, M. T., Padgett, W., and Daly, J. W. (1986) Life Sci. 39, 743-750.

(9) Ukena, D., Olsson, R. A., and Daly, J. W. (1987) Can. J. Physiol. Pharmacol., in press.

(10) London, C. , Cooper, D. M. F., and Wolff, J. (1980) Proc. Natl. Acad. Sci. USA 77, 2551-2554. (11) Davies, L. P., Chow, S. C., Sherrit, J. H., Brown, D. J., and Johnston, G. A. R. (1984) Life Sci. 34, 2117-2128.

(12) Williams, M., Risley, E. A., and Huff, J. R. (1981) Can. J. Physiol. Pharmacol. 59, 897-900.

(13) Psychoyos, S., Ford, C. J., and Phillios, M. A. (1982) Biochem. Pharmacol. 31, 1441-1442.

(14) Glennon, R. A., Tojani-Butt, S. M., Padgett, W., and Daly, J. W. (1984) J. Med. Chem. 27, 1364-1367.

(15) Daly, J. W., Padgett, W., Thompson, R. D., Kusachi, S., Bugni, W. J., and Olsson, R. A. (1986) Biochem. Pharmacol 35, 2467-2481.

(16) Ukena, D., Jacobson, K. A., Padgett, W. L., Ayala, C., Shamim, M. T., Kirk, K. L., Olsson R. A., and Daly, J. W. (1986) FEBS Lett. 209, 122-128.

(17) Kuzachi, S., Thompson, R. D., Bugni, W. J., Yamada, N., and Olsson, R. A. (1985) J. Med. Chem. 28, 1636-1643, While particular embodiments of the invention have been described it will be understood of course that the invention is not limited thereto since many obvious modifications can be made and it is intended to include within this invention any such modifications as will fall within the scope of the appended claims.

What is claimed is:

1. The method of antagonizing the adenosine receptor which comprises administering to a subject an effective amount of a compound selected from the group of compounds represented by the general formula

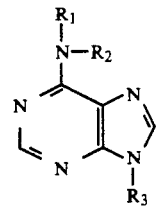

wherein R is selected from the group consisting of cycloalkyl radicals having from 3 to 7 ring carbon atoms, alkyl radicals having from 1 to 10 carbon atoms, aryl radicals having from 6 to 10 carbon atoms, aralkyl radicals having from 8 to 10 carbon atoms and heteroatom substituted derivatives thereof wherein said heteroatom may be selected from the group consisting of halogen, nitrogen, phosphorus, sulfur and oxygen; $R_2$ may be hydrogen or R and $R_3$ is an alkyl group comprising from 1 to 4 carbon atoms.

2. The method of claim 1 wherein said subject is a human.

3. The method of claim 1 wherein R is norbornyl.

4. The method of claim 3 wherein the adenosine receptor is the $A_1$ adenosine receptor.

* * * * *

UNITED STATES PATENT AND TRADEMARK OFFICE
CERTIFICATE OF CORRECTION

PATENT NO. : 5,066,655
DATED : Nov. 19, 1991
INVENTOR(S) : Ray A. Olsson

It is certified that error appears in the above-indentified patent and that said Letters Patent is hereby corrected as shown below:

Column 10, Claim 1, lines 10-20, that portion of the formula reading "$R_1$" should read --R--.

Signed and Sealed this

Eighth Day of August, 1995

Attest:

BRUCE LEHMAN

Attesting Officer
Commissioner of Patents and Trademarks